US005777902A

United States Patent [19]

Ono et al.

[11] Patent Number: 5,777,902
[45] Date of Patent: Jul. 7, 1998

[54] ANALYZER

[75] Inventors: Takayuki Ono; Kiyotoshi Mori, both of Hitachinaka, Japan

[73] Assignee: Hitachi, Ltd., Tokyo, Japan

[21] Appl. No.: 743,412

[22] Filed: Nov. 1, 1996

Related U.S. Application Data

[63] Continuation of Ser. No. 371,325, Jan. 11, 1995, abandoned.

[30] Foreign Application Priority Data

Mar. 16, 1994 [JP] Japan .................................. 6-045362

[51] Int. Cl.$^6$ ........................................................ G06F 17/40
[52] U.S. Cl. ........................... 364/579; 70/263; 235/375; 340/825.31
[58] Field of Search ..................... 340/825.31, 825.34; 364/579, 580; 70/262, 263, 264; 235/375

[56] References Cited

U.S. PATENT DOCUMENTS

| | | | |
|---|---|---|---|
| 4,812,994 | 3/1989 | Taylor et al. | 340/825.31 X |
| 4,873,633 | 10/1989 | Mezei et al. | 356/39 X |
| 4,887,292 | 12/1989 | Barrett et al. | 340/825.31 X |
| 5,068,798 | 11/1991 | Heath et al. | 364/497 |
| 5,365,587 | 11/1994 | Campbell et al. | 380/25 |
| 5,408,536 | 4/1995 | Lemelson | 340/825.31 X |
| 5,671,281 | 9/1997 | Campbell et al. | 380/25 |

FOREIGN PATENT DOCUMENTS 1-250758  10/1989  Japan .

OTHER PUBLICATIONS

International Laboratory, Apr. 1900, pp. 24, 26, 28, 30. "A Lims Spectrophotometer Interface" by N. Birnbaum, J. Hins, J. Farkas, and P. Cruz.

Nach. Chem. Tech. Lab. 40 (1992), No. 4, pp. 454–458 Chemis and Computer.

International Laboratory, Nov./Dec. 1992, pp. 21–26 "Benefits of client/server computing for analytical laboratoris" by Artie Green.

GIT Fachz. Lab. Oct. 1993, pp. 881–888, Laboratory Information Management Systems, Tools in Quality Assurance, by H. H. Majer , Dusseldorf.

JP 63-179 257 A. In: Patents Abstract of Japan, Sec. P., vol. 12, (1988), No. 456(P-793).

*Primary Examiner*—Edward R. Cosimano
*Attorney, Agent, or Firm*—Kenyon & Kenyon

[57] ABSTRACT

An analyzer constituted by a combination of a plurality of specific units selected from a large number of units, the analyzer includes a controller which allows, in response to an inputted user identification code of a user, the user to use a plurality of units registered in advance in a user file corresponding to the user identification code and which manages respective unit identification numbers of the units to be used. The analyzer further includes an output device which outputs the user identification code, the unit identification numbers of the units to be used and the date of measurement together with results of analysis.

6 Claims, 8 Drawing Sheets

FIG. 3

| NUMBERS OF REGISTERED IDs |
|---|
| $ID_1$ |
| $ID_2$ |
| ⋮ |
| $ID_n$ |

FIG. 4

| NUMBER OF USER FILES |
|---|
| USER FILE 1 CORRESPONDING TO $ID_1$ |
| USER FILE 2 CORRESPONDING TO $ID_2$ |
| ⋮ |
| USER FILE n CORRESPONDING TO $ID_n$ |

FIG. 5

| MEASUREMENT CONDITION DIRECTORY |
| --- |
| DEVICE CONDITION DIRECTORY |
| ANALYSIS DATA DIRECTORY |
| ANALYSIS RESULT DIRECTORY |
| NAME OF CHROMATOGRAPHIC UNIT SYSTEM 1 |
| PERMISSION FLAG OF CHROMATOGRAPHIC UNIT SYSTEM 1 |
| NAME OF UNIT 1 IN CHROMATOGRAPHIC UNIT SYSTEM 1 |
| PERMISSION FLAG OF UNIT 1 IN CHROMATOGRAPHIC UNIT SYSTEM 1 |
| ⋮ |
| NAME OF CHROMATOGRAPHIC UNIT SYSTEM N |
| ⋮ |
| PERMISSION FLAG OF UNIT M IN CHROMATOGRAPHIC UNIT SYSTEM N |

FIG. 6

| |
|---|
| ID |
| NUMBER m OF AVAILABLE CHROMATOGRAPHIC UNIT SYSTEM |
| ADDRESS INDICATING PECULIAR NUMBER OF AVAILABLE CHROMATOGRAPHIC UNIT SYTEM m(1) |
| ⋮ |
| ADDRESS INDICATING PECULIAR NUMBER OF AVAILABLE CHROMATOGRAPHIC UNIT SYTEM m(k) |
| PECULIAR NUMBER OF AVAILABLE CHROMATOGRAPHIC UNIT SYTEM m(1) |
| PECULIAR NUMBER OF AVAILABLE UNIT 1 IN CHROMATOGRAPHIC UNIT SYSTEM m(1) |
| ⋮ |
| PECULIAR NUMBER OF AVAILABLE UNIT j IN CHROMATOGRAPHIC UNIT SYSTEM m(1) |
| ⋮ |
| PECULIAR NUMBER OF AVAILABLE CHROMATOGRAPHIC UNIT SYTEM m(k) |
| PECULIAR NUMBER OF AVAILABLE UNIT 1 IN CHROMATOGRAPHIC UNIT SYSTEM m(k) |
| ⋮ |
| PECULIAR NUMBER OF AVAILABLE UNIT $l$ IN CHROMATOGRAPHIC UNIT SYSTEM m(k) |

FIG. 9

| ANALYSIS REPORT | 92.11.21 |

ID : S9682354
ANALYST NAME : A.O
CHROMATOGRAPHIC SYSTEM NAME 1 (PECULIAR No.) : SYSTEM A
                      UNIT NAME 1 (PECULIAR No.) : P4287206
                                  2 (PECULIAR No.) : A9134021
                                  3 (PECULIAR No.) : D3460037
                                  4 (PECULIAR No.) : O5093224
CHROMATOGRAPHIC SYSTEM NAME 2 (PECULIAR No.) : SYSTEM B
                      UNIT NAME 1 (PECULIAR No.) : P4287204
                                  2 (PECULIAR No.) : P4287205
                                  3 (PECULIAR No.) : P4287207
                                  4 (PECULIAR No.) : A9134020
                                  5 (PECULIAR No.) : D3460037
                                  6 (PECULIAR No.) : D3450009
                                  7 (PECULIAR No.) : O5093225

DEVICE CONDITIONS
  •
  •
  •

MEASUREMENT CONDITIONS
  •
  •
  •

ANALYSIS DATA
  •
  •
  •

ANALYSIS RESULTS
  •
  •
  •

P.1

ANALYZER

This is a continuation of application Ser. No. 08/371,325 filed 11 Jan. 1995, now abandoned.

BACKGROUND OF THE INVENTION

The present invention relates to an analyzer constituted by a combination of a plurality of processing element units.

An analyzer using ID codes for identifying users respectively to protect analysis data of samples is described in JP-A-1-250758. That is, JP-A-1-250758 discloses the features that multistageous functions capable of being operated in accordance with the levels of respective users are set so that functions enabled for a user to operate are indicated on a display when the user inputs the user's ID code and that the user confirms the enabled functions from the indication on the display and carries out a necessary operation on the basis of the enabled function to thereby complete the processing.

According to JP-A-1-250758, in an analyzer used by a user, the user can use only the functions enables for him/her so that data can be protected. In the case of an analyzer such as a liquid chromatographic analyzer in which a combination of processing element units such as column ovens, detectors, etc. must be changed by a user in accordance with the kind of an analysis sample to be measured, however, it is difficult to confirm the cause of a doubt in reliability in the results of analysis only by application of the thought disclosed in JP-A-1-250758.

SUMMARY OF THE INVENTION

An object of the present invention is to provide an analyzer in which it is possible to obtain an output useful for confirmation of reliability in the results of analysis through identification of a user in the case of using an analyzer which is constituted by a combination of a plurality of processing element units.

The foregoing object of the present invention is achieved by an analyzer which is constituted by a combination of a plurality of specific units selected from a large number of units and which comprises: a controller which allows, in response to an inputted user identification code of a user, the user to use a plurality of units registered in advance in a user file corresponding to the user identification code and which manages respective unit identification numbers of the units to be used; and an output device which outputs the user identification code, the unit identification numbers of the units to be used and the date of measurement together with the results of analysis.

Overall management of the analyzer is made by a system manager independent of respective users. The system manager determines a user permitted to use the analyzer and prepares a user file corresponding to the user. The individual user file thus prepared has areas for storing sample measurement conditions, names of processing element units enabled to be used, and so on. All the user files are stored in a controller. Each of the user files has such contents that permit only the use of processing element units required by a user identified with a user identification code (ID) assigned to the user.

The analyzer per se has a plurality of processing element units having different processing functions. For example, in the case of a chromatographic analyzer, the analyzer has, as its processing units, a liquid feeding pump system, an automatic sampler system, a separation column oven system, and so on. Processing functions of each system have a plurality of processing element units different in processing capacity and processing format. The analyzer is constituted such that the processing element units enabled to use for a user from respective processing functions on the basis of a user file of the user are selectively operated and the selected processing element units are connected or related to each other so that analysis operation in accordance with the user can be carried out by the user per se.

When a user inputs an identification code (ID) assigned to the user, a specific combination of processing element units is determined by a controller in accordance with the contents of a user file corresponding to the ID. In this case, respective unit identification numbers (numbers peculiar to the respective units) are transferred to the controller individually from the respective processing element units enabled to use for the user and registered in the controller. That is, the unit identification numbers of the respective units to be used are managed by the controller. When a sample to be measured is analyzed by the combination of units enabled to use in accordance with the user identification code, the results of analysis are preserved in specific areas of the user file. In the case where there is an instruction to output the results of analysis, the analysis results, the user identification code, the respective unit identification numbers of the units used and the date of measurement are indicated on a display or on printing paper. From this indication, a user or a system manager can make a confirmation in that by what combination of units, by whom, and when, the results of analysis about the object sample were obtained.

BRIEF DESCRIPTION OF THE DRAWINGS

FIG. 3 shows an example of a user identification code management table;

FIG. 4 shows an example of a user file management table;

FIG. 5 shows an example of a user file;

FIG. 6 shows an example of an ID file;

FIG. 9 is a view showing an output example of the results of measurement.

DESCRIPTION OF THE PREFERRED EMBODIMENTS

Figure 1:
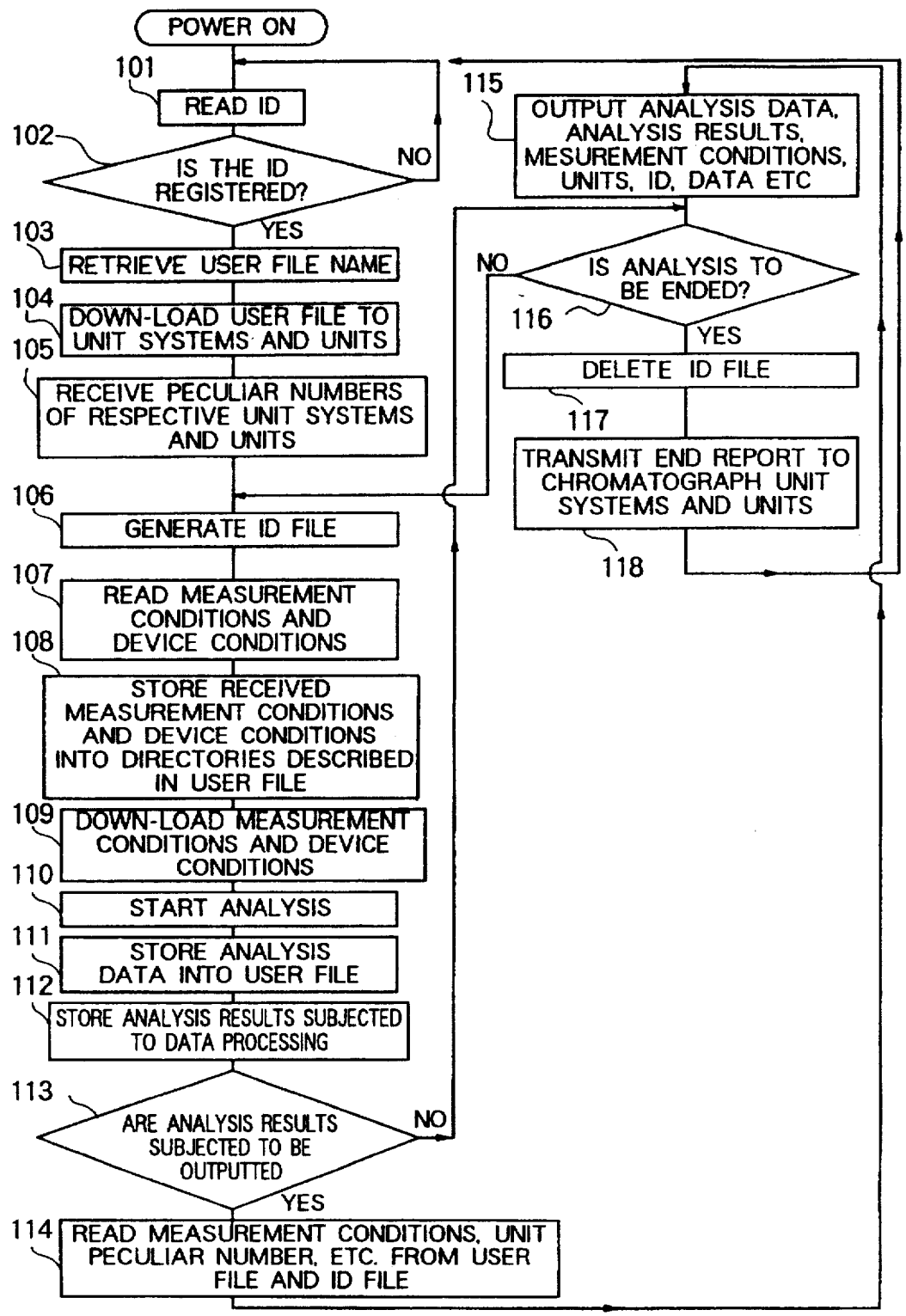
FIG. 1 is a flow chart for explaining a data processing operation in a liquid chromatographic analysis system as an embodiment of the present invention.

In a preferred embodiment of the present invention, the present invention is applied to a liquid chromatographic analyzer, but the application of the present invention is not limited thereto. For example, the present invention may be applied to the case where biochemical analysis functions, immunological analysis functions, electrolyte measurement functions, medicine measurement functions and so on are used selectively. The outline of a liquid chromatographic analysis system will be described below.

In the liquid chromatographic analysis system, the respective operations of a plurality of chromatographic analysis portions are managed by a data processing unit which acts as a controller. A system manager determines contents (analysis portions, processing element units, measurement method, etc.) to be enabled to use for each of users individually in accordance with a predetermined criterion, generates user files corresponding to the respective users in advance and stores those user files in the data processing unit in advance. Further, the system manager stores user identification codes (IDs) corresponding to the respective user files in the data processing unit in advance. The system manager determines the IDs so that the IDs have one-to-one correspondence to the user files, that is, the same ID is not assigned to a plurality of users. A user who intends to conduct chromatographic analysis of an object sample inputs his/her own ID given by the system manager through an input portion of the data processing unit. Only in the case where the inputted ID is coincident with the ID stored in advance, the user is permitted to use this liquid chromatographic analysis system. In the case where the inputted ID is not coincident with the ID stored in advance, the user is not permitted to use this analysis system. Accordingly, the use of this analysis system is limited only to a user who is permitted by the system manager to use this analysis system. When a chromatographic analysis operation of an object sample is started by a user after the user is permitted to use the analysis system, a unit condition file and a measurement condition file which are to be set in the controller are not enabled to be set with respect to all the chromatographic analysis portions and all the processing element units but enabled to be set with respect to limited chromatographic analysis portions and processing element units which are described in a user exclusive file (ID file) temporarily generated by the controller.

When the ID inputted by the user is coincident with the ID stored in advance, a user file corresponding to the ID is retrieved in the inside of the data processing unit so that the user file is down-loaded to a plurality of chromatographic analysis portions containing various types of processing element units and to the respective processing element units. In the user file, there are described a directory for storing measurement conditions, a directory for storing analyzer conditions, a directory for storing analysis data, a directory for storing analysis results, names of chromatographic analysis portions and permission flags thereof, and names of processing element units constituting the respective chromatographic analysis portions and permission flags thereof. Incidentally, the directories for storing measurement conditions, analyzer conditions and measurement data respectively have one-to-one correspondence to the IDs. Accordingly, measurement conditions, analyzer conditions and measurement data of one user can be protected from other users having IDs different from the ID of the one user, so that the analysis data or the like of the one user can be prevented from being deleted by other users by mistake.

The chromatographic analysis portions and processing element units to which the user file is downloaded are enabled to operate or disabled from operating in accordance with information described in the corresponding user file. Chromatographic analysis portions and processing element units enabled to operate transfer peculiar numbers constituted by production numbers peculiar to them, and so on, to the data processing unit. Upon reception of those peculiar numbers, the data processing unit identifies the chromatographic analysis portions and processing element units and generates a temporary file (hereinafter referred to as "ID file") with respect to the analyst ID. In this ID file, there are described peculiar numbers of the chromatographic analysis portions and individual processing element units enabled to use for the user. In the case of outputting of analysis results to an output device, the peculiar numbers of the analysis portions and units described in the ID file are outputted together with the analyst ID, measurement conditions and measurement data.

The user sets desired measurement conditions and device conditions for the enabled processing element units or the like by using the setting display and pushes a measurement start key to make the liquid chromatographic analysis system start the analysis operation. A sample introduced into analysis portions constituted by the specific combination of processing element units from an automatic sampler selected in accordance with the user ID is decomposed by a selected separation column, so that component peaks are measured by a selected detector. Measurement data such as chromatographic peak data or chromatogram data corresponding to the components to be measured are transferred to the data processing unit and preserved in the analysis data directory of the corresponding user file. The measurement data are subjected to an arithmetic operation in the data processing unit, so that concentrations of the respective components are obtained as analysis results and preserved in the analysis result directory of the corresponding user file.

In the case where a user or a system manager wants to know analysis data with respect to a specific ID, the date of measurement, the user ID, the identification numbers (peculiar numbers) of respective chromatographic analysis portions used in the analysis, the identification numbers (peculiar numbers) of respective processing element units used in the analysis, individual device conditions, measurement conditions, analysis data, analysis results, and so on, are outputted to the output device as long as an outputting instruction is given to the data processing unit. The date of measurement is preserved in the analysis data directory and/or analysis result directory of the user file together with data and results. By the aforementioned configuration, the device used in the analysis, measurement conditions, device conditions, analysis data and analysis results are related to the user ID, so that reliability on analysis data and analysis results is improved. In addition, because analysis data and analysis results are preserved in the peculiar directories described in the user file, other analysts having different IDs cannot refer to the analysis data and analysis results so that there is no risk that the analysis data and analysis results may be altered.

Specific embodiments of the present invention will be described below with reference to the drawings.

Figure 7:
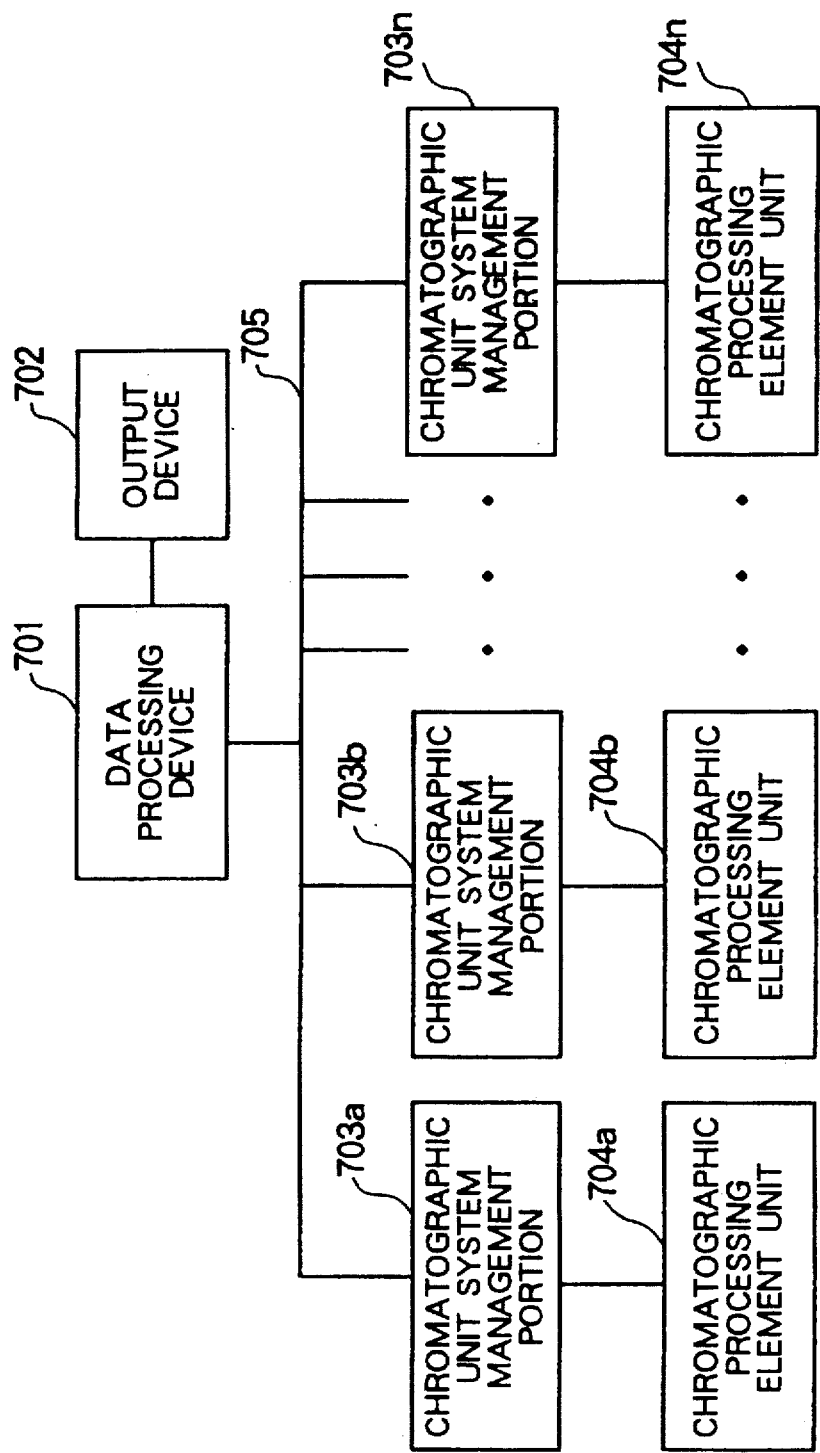
FIG. 7 is a schematic view showing the configuration of a liquid chromatographic analysis system to which the present invention is applied.

First, referring to FIG. 7, the configuration of the liquid chromatographic analysis system will be described. The reference numeral 701 designates a data processing unit; 702, an output device; 703a to 703n, chromatographic unit system management portions; 704a to 704n, chromatographic analysis portions having chromatographic processing element units; and 705, a communication line.

Figure 8:
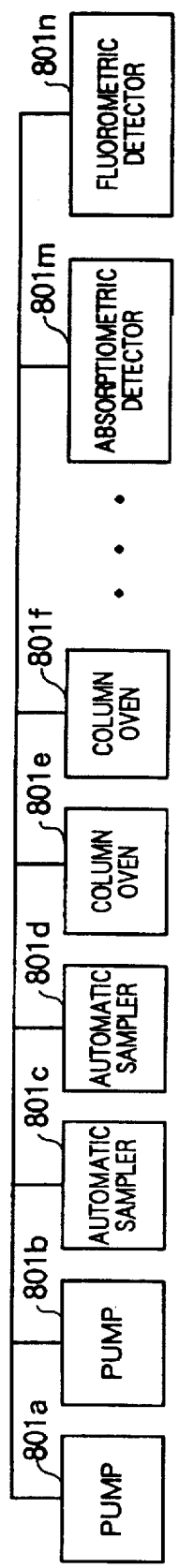
FIG. 8 is a diagram showing the configuration of the processing element units.

Referring next to FIG. 8, one chromatographic analysis portion will be described. The reference numerals 801a to 801n designate individual processing units, for example, the reference numerals 801a and 801b designate pumps capable of feeding different eluates respectively; 801c and 801d, automatic samplers having different processing capacities respectively; 801e and 801f, column ovens having different types of separation columns set respectively; and 801m and 801n, an absorptiometric detector and a fluorometric detector respectively.

Referring next to FIGS. 1 through 5, the operation of the liquid chromatographic analysis system shown in FIG. 7 will be described. A user, that is, an analyst who operates the analysis system, powers on this analysis system. By this power-on, the data processing unit stands by for inputting of a user ID. In a step 101, the analyst inputs a user ID given to the analyzer per se into the data processing unit 701. In a step 102, the data processing unit 701 collates the inputted ID with the ID registered by the system manager in advance. FIG. 3 shows an example of an ID management table in this case. IDs determined by the system manager are registered in this ID management table. This ID management table is stored in the data processing unit 701. If there is no coincidence in ID at this point of time, the situation of the routine goes back to the step 101 and the data processing unit 701 stands by for inputting of the next ID. Only in the case where there is coincidence in ID, the use of the analysis system is permitted and the situation of the routine goes to a step 103.

In the step 103, a user file name corresponding to the ID for which the use of the analysis system is permitted is retrieved from a user file management table as shown in FIG. 4. Then, in a step 104, a user file as shown in FIG. 5 is retrieved on the basis of the thus retrieved user file name and down-loaded to respective chromatographic unit system management portions 703a to 703n and to respective processing element units 801a to 801n. In this user file, there are described directory information for storing measurement conditions, device conditions, analysis data, and analysis results respectively, names of a plurality of chromatographic unit systems (names of chromatographic analysis portions) constituting the liquid chromatographic analysis system, names of processing element units constituting the respective chromatographic unit systems and flags indicating whether the analyst having the input ID can use chromatographic unit systems and processing element units respectively.

Figure 2:
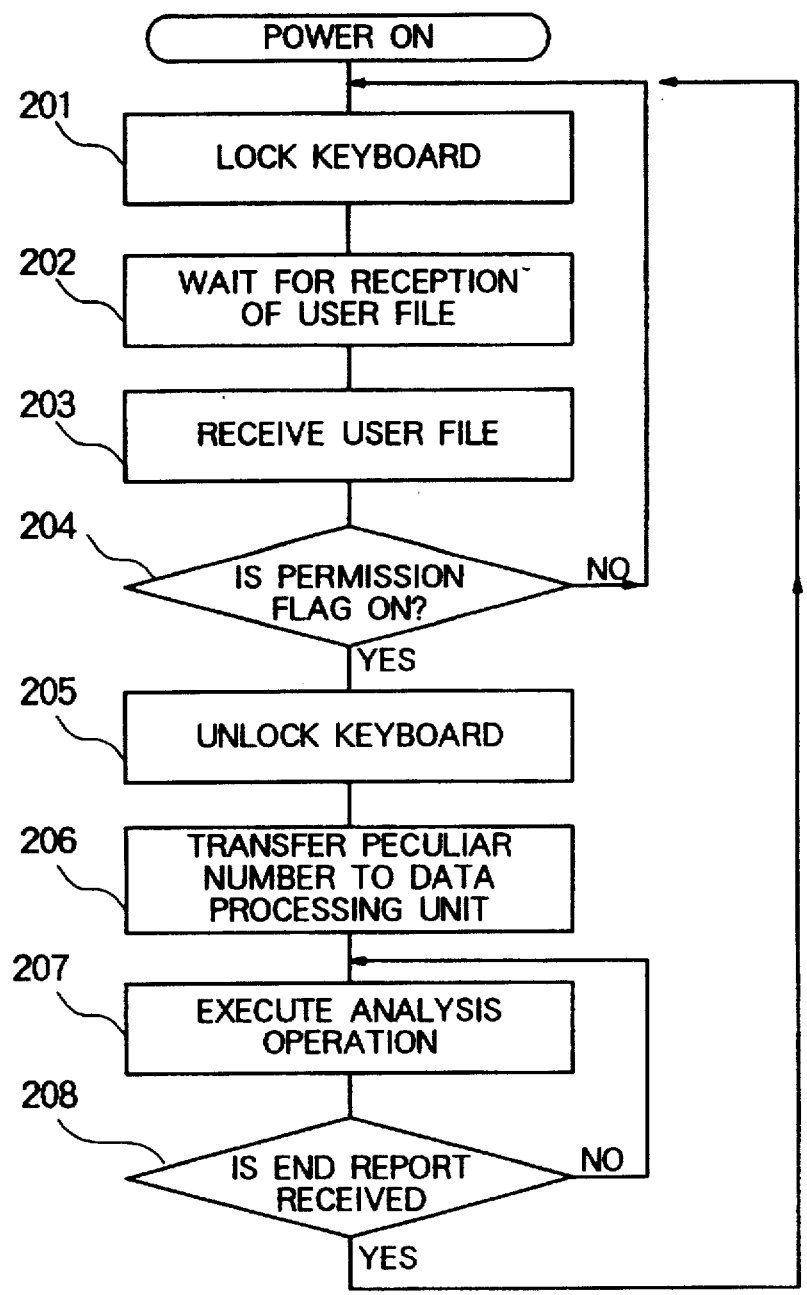
FIG. 2 is a flow chart for explaining an operation of a chromatographic analysis portion in FIG. 7.

Referring now to FIG. 2, the operation of chromatographic unit systems, that is, chromatographic analysis portions, and processing element units to which the user file is down-loaded will be described. In a step 201, at the moment of powering-on, an input portion such as a keyboard or the like is locked so that chromatographic unit system management portions and units constituting chromatographic unit systems are disabled from being controlled by the analyst. Then, in a step 202, chromatographic unit system management portions and units constituting chromatographic unit systems stand by for reception of a user file from the data processing unit. In a step 203, a user file is received. In a step 204, upon the reception of the user file, the chromatographic unit system management portions and the units constituting chromatographic unit systems retrieve the user file and refer to permission flags for their own devices. By the locking of the keyboard, the analyst can be prevented from operating by mistake. If the permission flag is determined not to be ON in step 204, the routine returns to step 201.

In a step 205, in the case where the permission flag is on, the input device such as the keyboard or the like is unlocked so that the analyst is permitted to use the device. Then, in a step 206, the chromatographic unit system management portions and the units transfer peculiar numbers constituted by production numbers their own devices, or the like, to the data processing unit 701. In a step 207, an analysis operation is executed in accordance with a control instruction, or the like, given by the data processing unit or the analyst. In a step 208, when a series of analysis operations are completed, a judgment is made as to whether an end report from the data processing unit is received or not. If the end report is not received, the situation of the routine goes back to the analysis operation step 207. On the contrary, when the end report is received, the situation of the routine goes back to the step 201.

The operation of the chromatographic unit systems and the chromatographic units subjected to downloading of the user file has been described above.

The description is now returned to FIG. 1. In a step 105, the data processing unit receives the peculiar numbers from the chromatographic unit system management portions and the respective units. In a step 106, upon the reception of the peculiar numbers from the chromatographic unit system management portions and the units constituting chromatographic unit systems, the data processing unit generates an ID file as shown in FIG. 6. This ID file is constituted by an ID, the number of chromatographic unit systems enabled to use for the analyst who inputs the ID, numbers peculiar to the chromatographic unit system management portions and numbers peculiar to the units constituting the chromatographic unit systems. Then, in a step 107, the data processing unit reads measurement conditions and device conditions from the directories described in the user file.

In a step 108, the analyst resets the device conditions and measurement conditions for starting analysis. When the setting is completed, the device conditions and measurement conditions are stored in the directories described in the user file. Then, in a step 109, the device conditions and measurement conditions stored in the directories described in the user file are down-loaded to the chromatographic unit system management portions and to the units. In a step 110, the analyst starts analysis in accordance with the set device conditions and measurement conditions. In a step 111, analysis data are collected from the chromatographic unit system management portions and the units constituting the chromatographic unit systems by the data processing unit and are stored in the analysis data storage directory designated in the user file.

In a step 112, the data processing unit 107 carries out an arithmetic operation upon the collected analysis data and stores the analysis results in the analysis result storage directory designated in the user file. In a step 113, the analyst designates whether analysis results are to be outputted or not. In the case where analysis results are to be outputted, the situation of the routine goes to a step 114. In the case where analysis results are not to be outputted, the situation of the routine goes to a step 116. In the case where analysis results are to be outputted in the step 114, measurement conditions, device conditions, analysis data and analysis results are read from the respective directories designated in the user file and the ID of the analyst, names of chromatographic unit systems enabled to use for the analyst and peculiar numbers thereof, and names of chromatographic units constituting the chromatographic unit systems and peculiar numbers thereof are read from the ID file.

In a step 115, the data processing unit 701 outputs to the output device the measurement conditions, device conditions, analysis data, analysis results, analyst ID, names of the chromatographic unit systems enabled to use for the analyst and peculiar numbers thereof, and names of the chromatographic units constituting the chromatographic unit systems and peculiar numbers thereof which have been read in the step 114, together with the data of measurement. FIG. 9 shows an example thereof. In a step 116, when a series of analysis operations are completed, the analyst designates whether the analysis is to be continued or not. In the case where the analysis is to be continued, the situation of the routine goes back to the step 106. In the case where the analysis is to be finished, the situation of the routine goes to a step 117. In the step 117, when the analyzer designates the termination of analysis, the data processing unit deletes the ID file generated on the basis of the ID of the analyst and the user file. In a step 118, the data processing unit transmits an end report to the chromatographic unit systems enabled to use for the analyst and to the units constituting the chromatographic unit systems. The routine then proceeds back to step 101 to wait to read another ID.

In the aforementioned embodiment, the points that by whom, when, and by use of what combination of processing elements, the analysis of an object sample was conducted can be made clear. Further, not only chromatographic systems enabled to use for an analyst and processing element units enabled to be used in the chromatographic systems are determined on the basis of the ID peculiar to the analyst but also the ID of the analyst and peculiar numbers such as production numbers of the chromatographic units used for measurement, or the like, in addition to analysis data are outputted as analysis results, so that reliability on the analysis data and analysis results can be established. Furthermore, measurement conditions and analysis data can be protected from other users by the ID peculiar to the analyst.

In the aforementioned embodiment, the data with respect to points that by whom, when, and by use of what combination of processing elements, the analysis of an object sample was conducted are outputted so that the aforementioned embodiment is very useful for confirmation of reliability on analysis results through identification of users.

What is claimed is:

1. An automatic analyzer comprising:

a) a plurality of analysis portions each having a plurality of processing element units;

b) a data processing unit including storage; and c) an output device, wherein:

d) a unit identification code is assigned to each of said analysis portions and to each of said processing element units, said unit identification code being stored in said data processing unit;

e) a user identification code corresponding to a user is stored in said data processing unit;

f) unit identification codes corresponding to particular analysis portions and to particular processing element units, which the user is permitted to use for executing an analysis operation, are assigned to each of said user identification codes in said data processing unit; and g) analysis results, and identification of analysis portions and processing element units used for analysis are output by said data processing unit to said output device after analysis operation is completed.

2. An analyzer system according to claim 1 and further including an area in said data processing unit storing analyzed results with the identification numbers of the analyzers used for the analysis and the user identification code.

3. An analyzer system according to claim 1, said data processing unit outputs analyzed results with the identification numbers of the analyzers used for the analysis and the user identification code.

4. An analyzer system according to claim 1, wherein an area for storing information of the user identification code and identification number for analyzer which is allowed for the user to use is provided in said data processing unit.

5. An analyzer system according to claim 4 and further including an area in said data processing unit storing analyzed results with the identification numbers of the analyzers used for the analysis and the user identification code.

6. An analyzer system according to claim 4, said data processing unit outputs analyzed results with the identification numbers of the analyzers used for the analysis and the user identification code.

* * * * *